United States Patent
Urban et al.

Patent Number: 5,876,016
Date of Patent: Mar. 2, 1999

[54] APPARATUS AND METHOD TO ELEVATE AN INFUSION SOURCE

[76] Inventors: Theodore A. Urban, 71 Stephen St., Levittown, N.Y. 11756; Matthew A. Franks, 211 Princeton Ct., Allenwood, N.J. 08720

[21] Appl. No.: 856,066

[22] Filed: May 14, 1997

[51] Int. Cl.$^6$ .................................................. A61M 5/00
[52] U.S. Cl. ........................................ 248/159; 604/246
[58] Field of Search ................................. 248/121, 125, 248/129, 158, 159, 176.1; 604/246

[56] References Cited

U.S. PATENT DOCUMENTS

| | | | |
|---|---|---|---|
| 49,145 | 8/1865 | Palmenberg | 248/159 |
| 396,321 | 1/1889 | Baird | 248/159 X |
| 1,781,203 | 11/1930 | Teleki | 248/159 X |
| 2,696,963 | 12/1954 | Shepherd | 248/229 |
| 2,887,988 | 5/1959 | Cottongim | 248/159 |
| 2,957,187 | 10/1960 | Raia . | |
| 3,285,554 | 11/1966 | Voelkerding | 248/121 |
| 3,690,610 | 9/1972 | Peirce | 248/159 |
| 3,835,486 | 9/1974 | Benoit et al. | 248/161 X |
| 3,995,796 | 12/1976 | Kline | 248/121 |
| 4,625,937 | 12/1986 | Haase | 248/159 X |
| 5,026,393 | 6/1991 | Mackool . | |
| 5,084,009 | 1/1992 | Mackool . | |
| 5,112,019 | 5/1992 | Metzler et al. | 248/125.1 X |
| 5,222,946 | 6/1993 | Kamen | 248/121 X |
| 5,286,256 | 2/1994 | Mackool . | |
| 5,319,816 | 6/1994 | Ruehl | 248/121 X |
| 5,354,265 | 10/1994 | Mackool . | |
| 5,366,191 | 11/1994 | Schmuhl | 248/125 |
| 5,505,693 | 4/1996 | Mackool . | |
| 5,569,188 | 10/1996 | Mackool . | |

Primary Examiner—Derek J. Berger
Attorney, Agent, or Firm—Cobrin & Gittes

[57] ABSTRACT

An apparatus and method to elevate an infusion source, the pole of a control unit is increased by about thirty-two (32) cm to increase the height of an infusion bottle attached to a hanger on the pole during ophthalmic surgery including that performed with a phacoemulsification surgical handpiece. The control unit being for irrigation and suction lines that lead to the phacoemulsification surgical handpiece used to conduct eye surgery.

22 Claims, 2 Drawing Sheets

APPARATUS AND METHOD TO ELEVATE AN INFUSION SOURCE

BACKGROUND OF THE INVENTION

1. Field of the Invention

The present invention relates to a pole used to extend the elevation of an infusion source that provides fluid during eye surgery.

2. Discussion of the Related Art

Intravenous poles with hangers are used to hang infusion bottles by health care facilities, ambulatory centers, hospitals, nursing homes and physicians in their offices. The ALCON 20000 LEGACY SERIES is used by physicians when performing ophthalmic or cataract surgery employing the MACKOOL SYSTEM™ as taught under one or more of the following: U.S. Pat. Nos. 5,026,393; 5,084,009; 5,286,256; 5,354,265, 5,505,693 and 5,569,188. Although the ALCON 20000 LEGACY unit has an intravenous pole incorporated or built into its base, the height of the pole is too short to satisfy the height requirements of the MACKOOL SYSTEM™ and/or procedures requiring vacuums of 250 mm or more, if the cassette of the unit is positioned at approximately eye level of the patient. For this reason, a separately standing intravenous pole is used to hang the infusion bottle at the appropriate height.

The ALCON 20000 LEGACY SERIES apparatus includes a base with a slot into which is fitted a cassette containing irrigation and suction lines that convey fluid to or from a phacoemulsification handpiece. The eye level of the patient whose eye is to be operated upon approximately corresponds to the elevation of the center of the cassette when the cassette is inserted into the slot. The cassette also contains valves in the lines to allow the flow rate through the lines to vary as desired by operating appropriate controls on the base via a foot switch.

The ALCON 20000 LEGACY SERIES also includes a telescoping pole of a maximum seventy-eight (78) cm in height and a hanger attached to the pole on which to hang an infusion bottle. The infusion bottle is hung upside down and is connected to the cassette in the base via a supply line. Accordingly, the flow rate and pressure of the liquid in the infusion bottle are limited based on the elevation of the infusion bottle and as regulated by the cassette valves.

The MACKOOL SYSTEM™ recommends placing the infusion bottle at a height, relative to the eye level of the patient, of 60–78 cm for purpose of avoiding portal occlusion while carrying out deliberate sculpting of the eye so the vacuum pressure being applied is about 20–40 mm Hg. The bottle height is then raised to 78–110 cm to carry out rapid sculpting (that employs portal occlusion) at about 250 mm Hg vacuum or higher, nucleus impaling at 250–350 mm Hg vacuum during a phaco chop, and nuclear segment removal at 250–350 mm Hg vacuum. Peripheral sculpting such as a one handed technique is carried out with the bottle height at 60–110 cm and the vacuum at 40–150 mm Hg. In all cases which employ the MACKOOL SYSTEM™ and all phacoemulsification procedures, the flow rate is 15 cc/mm, although for nuclear segment removal the flow rate may be increased up to 35 cc/mm.

In the absence of an apparatus to elevate the infusion bottle of the present invention, the MACKOOL SYSTEM™ is used with the ALCON 20000 LEGACY SERIES by hanging the infusion bottle to a separate IV pole at the appropriate height. Some measurement as to placement of the infusion bottle may be required because the exact location of the infusion bottle corresponding to eye level of the patient is not marked. The separate IV pole may either be at a fixed height or may be adjusted via a telescoping feature such as that described in U.S. Pat. No. 2,957,187 issued on Oct. 25, 1960 to Louis Raia entitled "Telescopic Stand", whose contents are incorporated herein by reference. Aside from this inconvenience in measurement, the need for a separate intravenous pole is in and of itself a burden on the surgeon or support facility in procuring it and finding space to place it.

A need exists to perform eye surgery according to the MACKOOL SYSTEM™ but without the inconvenience of relying on a separate IV pole to elevate the infusion bottle to the proper height. An increase of 32 cm in elevation increases intraocular pressure applied to irrigate the eye during eye surgery to satisfy the vacuum pressure demands of the MACKOOL SYSTEM™. A total of 110 cm is measured from the cassette in the base where the irrigation lines emerge (at approximately patient eye level) to the elevation of a stopper in the inverted top of the infusion bottle.

SUMMARY OF THE INVENTION

An aspect of the present invention is to increase the distance between an infusion source and eye level of a patient in a position to undergo eye surgery by extending the length of a pole. The infusion source hangs from the pole and the pole extends upwardly from an irrigation and suction line control unit, which controls fluid flow through an ophthalmic or phacoemulsification surgical handpiece. By increasing the height of the pole by 32 cm, the control unit becomes suitable for delivering a higher infusion pressure to inflate the eye as medically recommended for performing certain eye surgery techniques.

BRIEF DESCRIPTION OF THE DRAWINGS

For a better understanding of the present invention, reference is made to the following description and accompanying drawings, while the scope of the invention is set forth in the appended claims.

DESCRIPTION OF THE PREFERRED EMBODIMENT

Figure 1:
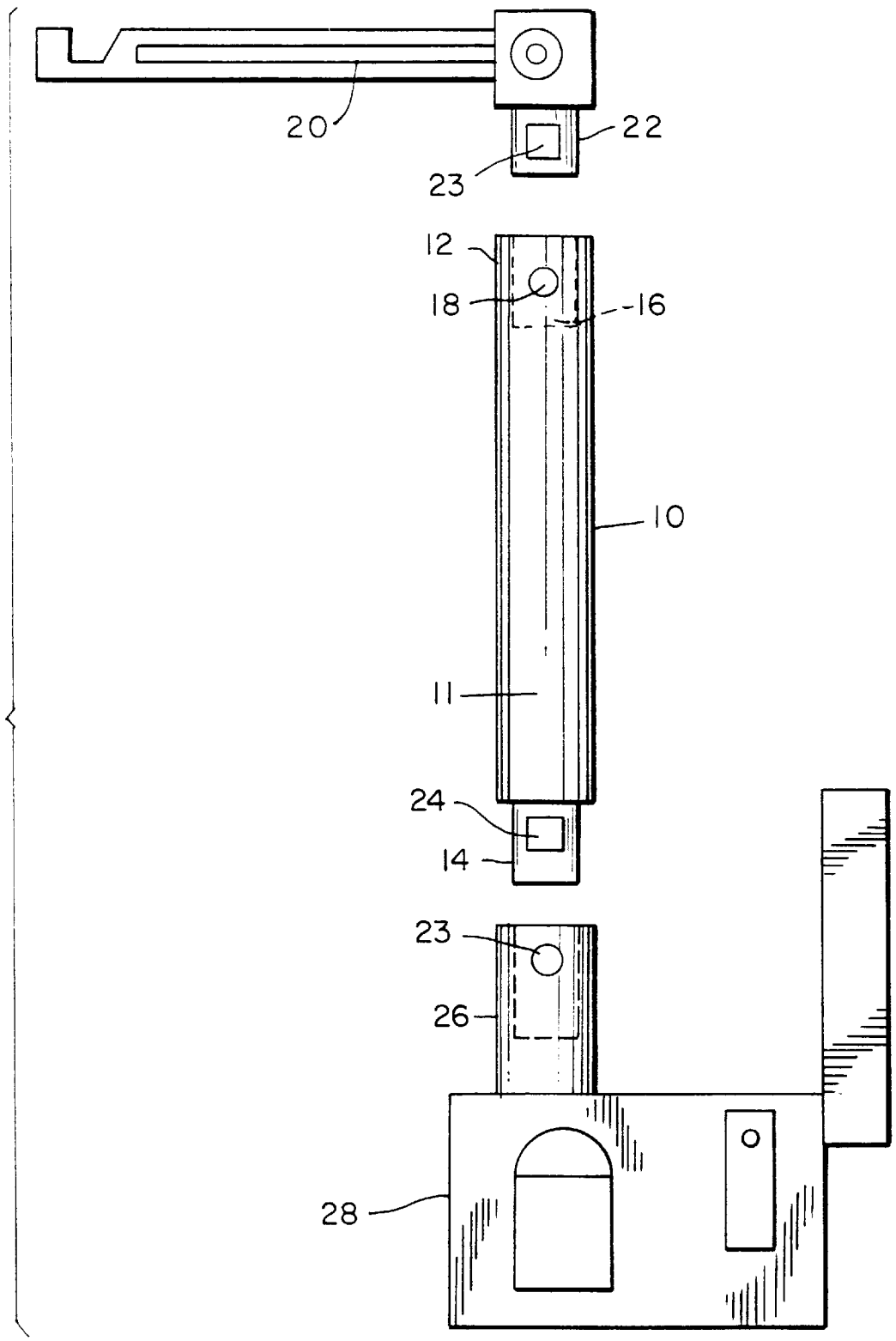
FIG. 1 shows a schematic representation of an exposed view of a pole adapter in accordance with the invention in position for assembly between a conventional hanger and conventional base of a control unit for irrigation and suction lines for use with a phacoemulsification handpiece.

Referring to the drawings, FIG. 1 shows a pole adapter 10 such as a solid body 11 with two opposite ends, one end being female 12, and the other being male 14. The female end 12 has an internal stopping element such as an internal ring 16. The internal ring 16 is closer to the female end 12 than to the male end 14. Such a construction may be formed by boring a solid body at the female end 12 to reach the level of the internal ring 16 and then boring the inner diameter of the ring by a distance at least the same as the tip of the male member to be inserted therein. An aperture 18 is formed through the wall of the solid body 11 in the area between the internal ring 16 and the edge of the female end 12. The aperture 18 is used to secure the pole to a conventional hanger 20, which is used to hang an infusion bottle. The hanger 20 has its own male end 22 that is inserted into the female end 12 of the solid body 11 and secured together at the aperture 18 with a fastener 23, such as an allen wrench set screw.

The solid body's male end 14 is of a smaller outer diameter than that of a stepped surface 24 situated between the male end 14 and the rest of the solid body 11 and may be formed by shaving off the periphery of the solid body 11 at the male end 14. A conventional base 28 has its own telescoping pole having a female connector 26, identical to the female open end 12, and may be secured to the pole adapter 10 after fitting the male end 14 of the solid body 11 into the female connector 26 by tightening a fastener 23, such as an allen wrench set screw through a fastening opening in the female connector 26.

Other conventional fastening techniques other than a set screw may be used instead, such as bolts, welds, adhesives, sliding collars, etc. The solid body 11 may instead be hollow or tubular. Also, its outer diameter may be smaller than or larger than or the same as that of its ends. While the solid body 11 is shown with a circular outer diameter, it may of course have any other type of geometric shape instead, such as oval, square, triangular, hexagonal, or any other polygonal shape. The preferable construction of the pole adapter is stainless steel, although other types of materials which are comparably resistant to inadvertent breakage will suffice, such as other types of steels, metals, plastics or wood.

Figure 2:
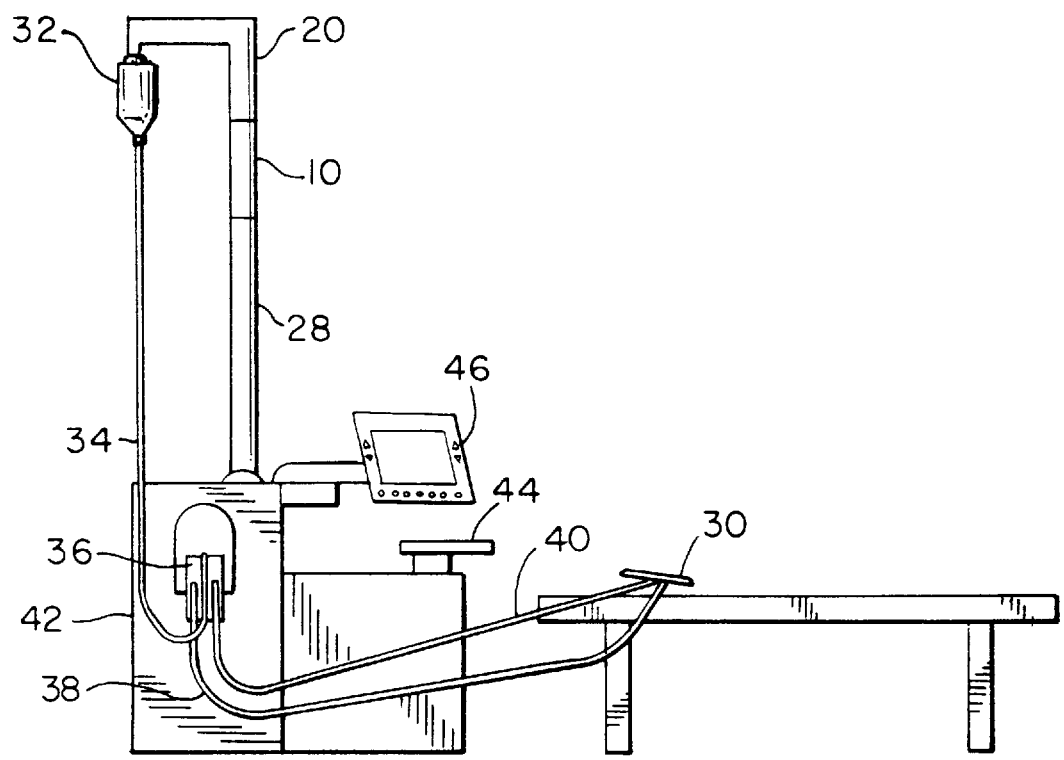
FIG. 2 shows a side elevational view of a conventional control unit for irrigation and suction lines for use with a phacoemulsification handpiece with the inserted pole adapter.

FIG. 2 depicts a conventional control unit for irrigation and suction lines leading to an ophthalmic or phacoemulsification surgical handpiece with the inserted pole adapter. In a known manner, the phacoemulsification surgical handpiece 30 is used to provide irrigation to the eye for inflation and to suction out tissue fragments cut by vibratory action imparted against the tissue by the tip of the handpiece 30. The control unit is exemplified by the ALCON 20000 LEGACY SERIES apparatus utilizing the MACKOOL SYSTEM™. The pole adapter 10 is connected at the bottom to the conventional base 28 and at the top to a conventional hanger 20. An infusion bottle 32 is hanging, inverted, from the conventional hanger 20. Attached to the infusion bottle 32 is a supply line 34 which is connected to a cassette 36, from which emerge irrigation and suction lines 38 and 40 that lead to any conventional phacoemulsification handpiece 30, although preferably of the types recommended for use with the MACKOOL SYSTEM™. The cassette 36 interacts with the computer base 42 controlled by the remote control 44 to enable a display on the computer screen with controls/selectors 46 of various flow characteristics in the irrigation and suction lines 38 and 40.

No matter what choice of construction of extension member(s) that project from the base to the hanger, the intent is to encompass the extension member being of a dimension such that a distance of between 79 and 140 centimeters is found between the stopper level of the infusion bottle 32, which is hanging from the hanger 20, and the eye level of the patient, which corresponds to where the irrigation and suction lines 38 and 40 enter the cassette 36 of the conventional base 28. The extension member(s) may be a single piece construction or multiple segments fitted together end to end. The extension members may include telescoping elements whose movements relative to each other vary the distance.

The extension member(s) may themselves reach beyond this distance condition within the range of 79 to 140 centimeters, as long as the hanger is hung at the appropriate level to satisfy this distance condition. Alternatively, the extension member(s) may be shorter provided the hanger is of a construction that it raises the infusion bottle to fall within this distance condition. The optimal distance condition is between 95 and 120 centimeters to provide a sufficient level of fluid pressure. Further, the extension member (s) are to be supported by the conventional base 28, as opposed to being a stand alone unit. In this context, it may extend upwardly from the top of the conventional base 28 or from the sides. The length of the pole adaptor 10 is between about 1 cm to about 62 cm.

While the foregoing description and drawings represent the preferred embodiments of the present invention, it will be understood that various changes and modifications may be made without departing from the spirit and scope of the present invention.

What is claimed is:

1. An apparatus to elevate an infusion source, comprising:
   an infusion source;
   an irrigation tubular element extending from said infusion source to channel fluid therethrough;
   a base having an area accommodating said irrigation tubular element, said irrigation tubular element channeling the fluid to flow from the infusion source to said area and then in a direction away from said base;
   an extension member extending from said base;
   a pole adaptor; and
   a hanger spaced from said base and holding said infusion source at an elevation higher than that of said area of said base, said pole adaptor being arranged between said hanger and said extension member to space apart said hanger from said base so that an elevational difference between said infusion source and said area of said base is between 79 cm and 140 cm.

2. An apparatus as in claim 1, wherein said pole adaptor extends in an upright position with said infusion source at a higher elevation than said base so that said distance provides adequate infusion delivery for at least 250 mm Hg of vacuum.

3. An apparatus as in claim 1, wherein said pole adaptor has a length between opposite end portions of about 1 cm to about 62 cm.

4. An apparatus as in claim 1, further comprising a phacoemulsification surgical instrument, connected between said irrigation tubular element and a suction tubular element.

5. An apparatus as in claim 1, further comprising a cassette in the area, said irrigation tubular element being connected to said cassette.

6. An apparatus as in claim 5, further comprising irrigation and suction lines attached to said cassette.

7. An apparatus as in claim 1, wherein said base and hanger each have respective connection areas, said pole adaptor having opposite ends each configured to connect in a complementary manner to respective ones of the connection areas of said base and hanger.

8. A method to elevate an infusion source, comprising the steps of:
   channeling fluid to flow from an infusion source through an irrigation tubular element;
   accommodating said irrigation tubular element in an area of a base, said irrigation tubular element channeling the fluid to flow from the infusion source to said area and then in a direction away from said base;
   holding the infusion source by the hanger at an elevation higher than that of said area of said base;

extending an extension member from said base; and arranging a pole adaptor between said extension member and the hanger to space apart said hanger from said base an elevational difference between said infusion source and said area of said base is between 79 cm and 140 cm.

9. A method as in claim 8, wherein the step of extending includes extending said extension member in an upright position with said infusion source at a higher elevation than said base so that said distance provides adequate infusion delivery for at least 250 mm Hg of vacuum.

10. A method as in claim 8, wherein said pole adaptor has a length between opposite end portions of about 1 cm to about 62 cm.

11. A method as in claim 8, further comprising the step of connecting said irrigation tubular element and a suction tubular element to a phacoemulsification instrument.

12. A method as in claim 8, wherein said base and hanger each have respective connection areas, said pole adaptor having opposite ends, further comprising the step of connecting the ends in a complementary manner to respective ones of the connection areas of said base and hanger.

13. An apparatus to elevate an infusion source, comprising:

an infusion source;

an irrigation tubular element extending from said infusion source to channel fluid therethrough;

a base having an area accommodating said irrigation tubular element, said irrigation tubular element channeling the fluid to flow from the infusion source to said area and then in a direction away from said base;

at least one extension member extending from said base;

a pole adaptor; and a hanger spaced from said area of said base and holding said infusion source at an elevation higher than said area of said base, said pole adaptor being arranged between said hanger and said extension member to space said hanger and base apart so that an elevational difference between said infusion source and said area of said base is sufficient to provide adequate infusion delivery from the infusion source to said area of said base of at least 250 mm Hg of vacuum.

14. An apparatus as in claim 13, wherein said pole adaptor has a length between opposite end portions of about 1 cm to about 62 cm.

15. An apparatus as in claim 13, further comprising a cassette in said area of said base and being connected to the irrigation tubular element, a phacoemulsification surgical instrument, and irrigation and suction lines connected to said phacoemulsification instrument and to said cassette.

16. An apparatus as in claim 13, further comprising a cassette in said area of said base, the irrigation tubular element being connected to said cassette.

17. An apparatus as in claim 16, further comprising irrigation and suction lines attached to said cassette.

18. An apparatus as in claim 13, wherein said base and hanger each have respective connection areas, said pole adaptor having opposite ends each configured to connect in a complementary manner to respective ones of the connection areas of said base and hanger.

19. A method to elevate an infusion source, comprising the steps of:

channeling fluid to flow from an infusion source through an irrigation tubular element;

accommodating said irrigation tubular element in an area of a base, said irrigation tubular element channeling the fluid to flow from the infusion source to said area of said base and then in a direction away from said base;

holding an infusion source with a hanger at an elevation higher than said area of said base;

extending at least one extension member from said base;

arranging a pole adaptor between said extension member and said hanger to space apart said hanger and said base so as that an elevational difference between said infusion source and said area of said base is sufficient to provide adequate infusion delivery from the infusion source to said area of said base of at least 250 mm Hg of vacuum.

20. A method as in claim 19, wherein said pole adaptor has a length between opposite end portions of about 1 cm to about 62 cm.

21. A method as in claim 19, further comprising the step of connecting said irrigation tubular element and a suction tubular element to a phacoemulsification instrument.

22. A method as in claim 19, wherein said base and hanger each have respective connection areas, said pole adaptor having opposite ends, further comprising the step of connecting the ends in a complementary manner to respective ones of the connection areas of said base and hanger.

* * * * *